United States Patent [19]
Yaginuma et al.

[11] Patent Number: 5,423,219
[45] Date of Patent: Jun. 13, 1995

[54] DEFECTS DETECTION DEVICE FOR FUEL ROD WELDMENT

[75] Inventors: Yoshitaka Yaginuma; Yoji Koike, both of Tohkai, Japan

[73] Assignee: Mitsubishi Nuclear Fuel Co., Tokyo, Japan

[21] Appl. No.: 159,239

[22] Filed: Nov. 30, 1993

[30] Foreign Application Priority Data

Nov. 30, 1992 [JP] Japan .................. 4-321029

[51] Int. Cl.6 .............................................. G21C 17/10
[52] U.S. Cl. ........................................ 73/622; 376/252
[58] Field of Search ................................ 376/252, 245; 976/DIG. 232; 73/622, 637, 640, 644

[56] References Cited

U.S. PATENT DOCUMENTS 4,328,708  5/1982  Bagwell ........................ 73/622
5,066,452  11/1991  Hancock ........................ 376/252

FOREIGN PATENT DOCUMENTS 62-153743  7/1987  Japan .
62-153744  7/1987  Japan .
4-66896    3/1992  Japan .

Primary Examiner—Thomas P. Noland
Assistant Examiner—Christine K. Oda
Attorney, Agent, or Firm—Oblon, Spivak, McClelland, Maier & Neustadt

[57] ABSTRACT

A compact ultrasonic inspection device of high resolution and operating speed is presented for examining the defects in a welded section between the end plug and the fuel pipe. The welded fuel rod is inserted into an inspection section of a rotating member filled with water, and is held immovably. The rotating member, having a plurality of ultrasonic probes disposed around the periphery, is rotated around the axis of the fuel rod to examine the welded section.

13 Claims, 9 Drawing Sheets

DEFECTS DETECTION DEVICE FOR FUEL ROD WELDMENT

BACKGROUND OF THE INVENTION

1. Field of the Invention

The present invention relates to a device for ultrasonic detection techniques for the inspection of weld defects in a fuel rod weldment.

2. Technical Background

In general, a fuel rod for use in a light water pressurized reactor is made by packing fuel pellets inside a fuel pipe, and the ends of the fuel pipe are fitted with end plugs and the end plugs are joined to the ends of the fuel pipe by means of joining techniques such as the tungsten inert gas (TIG) welding. Further, there is a (gas) seal opening disposed on one of the two end plugs for filling the fuel pipe interior with an inert gas under pressure. The gas seal opening is sealed off, by joining methods such as TIG welding, so as to maintain the interior of the fuel pipe at a certain inert gas pressure.

Conventionally, the joints of the fuel rod welded as described above have been inspected non-destructively by X-ray transmission. However, the X-ray method is being superseded by the ultrasonic inspection method which is more compact in apparatus design and easier to handle.

The ultrasonic inspection apparatuses which have been available to date are based on scanning the entire circumferential periphery of the weld by moving the detection probe linearly in the longitudinal direction while turning the fuel rod. When examining the weld by moving the detection probe in the longitudinal direction while rotating the fuel rod, there are no problems when the examination is being carried out at a rough scanning pitch or at low speeds. However, when it is desired to carry out inspection at a faster operating speed or at a finer scanning pitch, it was necessary to increase the rotational speed of the fuel rod, which lends to high loads on the rod and insufficient processing time for obtaining proper inspection results.

SUMMARY OF THE INVENTION

The present invention was made in view of the technical background presented above, and the objective of achieving efficient inspection of the weld with an inspection device comprising: a rotating member freely rotatable around its rotation axis having an inspection section formed within for holding said fuel rod in place during inspection; a liquid supplying means for filling said liquid medium in said inspection section; a plurality of ultrasonic probes disposed on said rotating member having said inspection section.

According to the device of the above configuration, the fuel rod to be inspected is housed in the inspection section disposed in the rotating member which is filled with liquid, and the rotating member is rotated while ultrasonic inspection is being carried out with the probes disposed on the rotating member. Therefore, there is no need to rotate the fuel rod, and consequently, it is possible to inspect the welded section without imposing loads on the fuel rod, and the inspection process can be carried out more quickly and with higher resolution than with conventional inspection techniques. Furthermore, the inspection apparatus can be made compact, and automation of the inspection process is made easier. The maintenance operation can also be carried out easily.

Another aspect of the invention is that the fuel rod is held firmly while being inspected.

Still another aspect of the invention is that a transport device is provided to move the rotating member relative to the fuel rod along the rotation axis.

Still another aspect of the invention is that the fuel rod is held stably during the inspection by an immobile or more particularly a non-rotating lid member provided opposite to and in sliding contact with an opening section of said rotating member for supporting the fuel rod which passes through a through hole disposed on the immobile on non-rotating lid member.

Still another aspect is that the liquid is contained in the inspection section by a through hole provided with: a seal member which envelopes the fuel rod tightly; and a lid member which closes the through hole and is swingable inside the inspection section to open when a fuel rod is inserted through the through hole.

Still another aspect is that the inspection is carried out while circulating the liquid from the bottom to the top by liquid supply means disposed on the lower part of the immobile lid member, and a liquid collection means for collecting liquid flowing out of the inspection section is disposed on the upper portion of the inspection section disposed on the upper portion of the immobile lid support member, Still another aspect is that the liquid is supplied to the rotating member through a plurality of liquid flow passages provided on the rotating lid member on the outer periphery; and liquid supply passages are provided opposite to each of the liquid flow passage disposed on the lower part of the immobile lid member for supplying liquid to the inspection section of the rotating member; and liquid collection passages are provided on the upper part of the immobile lid member opposite to each of the liquid flow passages for collecting liquid flowing out of the inspection section of the rotating member; wherein the diameters of each of the liquid supply passages and liquid collection passages are larger than the distance between the two adjacent liquid flow passages.

BRIEF EXPLANATION OF THE DRAWINGS

FIG. 12 (b) is a probe for detecting defects in the seal section.

PREFERRED EMBODIMENT

Figure 1:
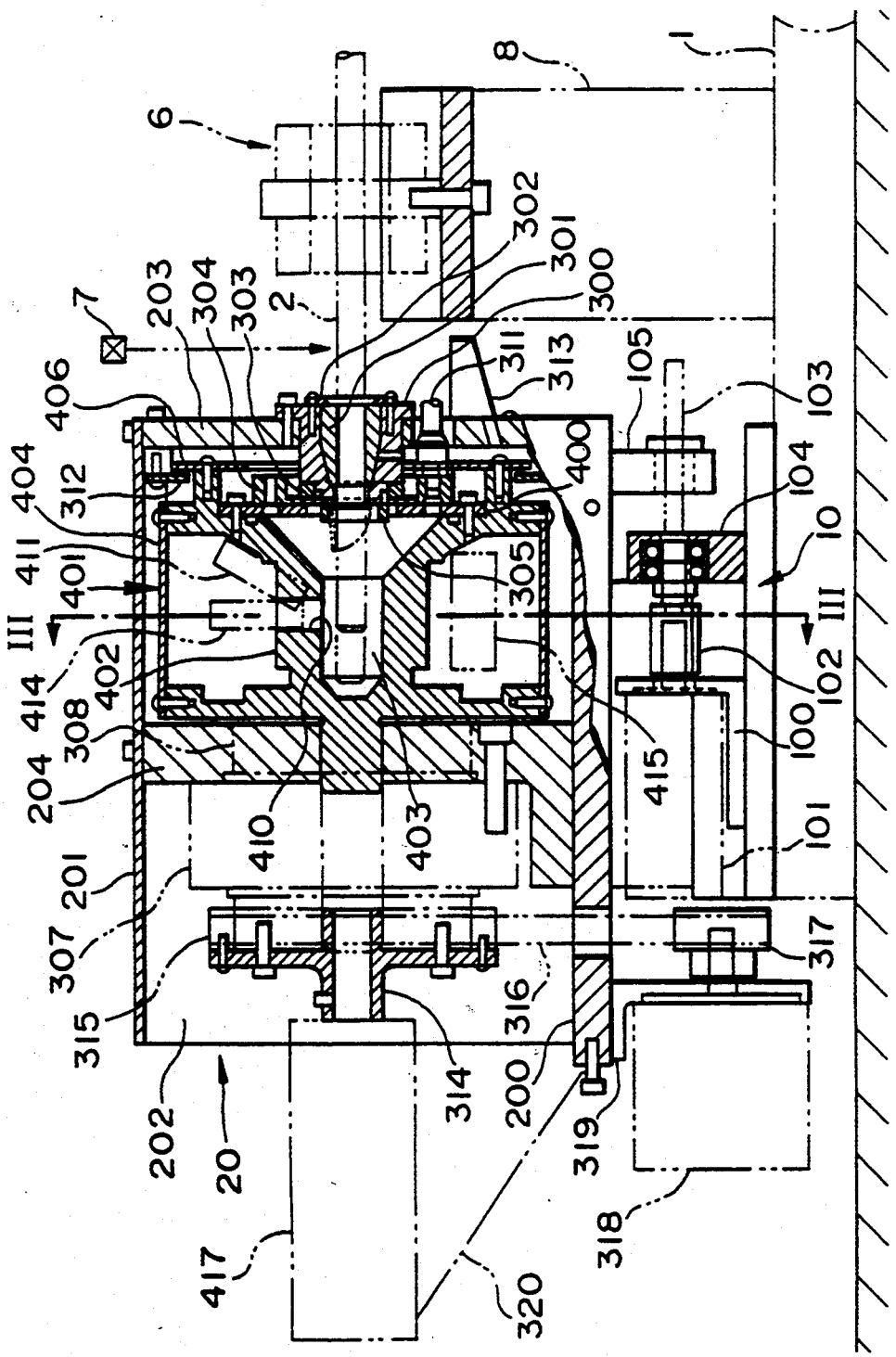
FIG. 1 is a cross sectional view of a first embodiment of the present invention.

The first embodiment will be explained below with reference to FIGS. 1 to 13.

In these drawings, the reference numeral 1 refers to a base, on which is disposed a transport device 10. The transport device 10 includes a transport motor 101 attached to the base 1 via an attachment member 100, and a ball screw shaft 103 attached to the rotation shaft of the transport motor 101 through a coupling 102, the ball screw shaft 103 is freely rotatably supported by the shaft support member 104, and is threaded to a nut member 105 fixed to the transport container 20.

By rotating the rotation axis of the transport motor 101, the transport container 20 moves along the ball screw shaft 103 (e.g. 3 mm) through the actions of the coupling 102, ball screw shaft 103 and the nut member 105.

The transport container 20 is configured as a box having a lower plate 200, an upper plate 201 and a pair of side plates 202, an end plate 203 with a through hole and a middle section plate 204 with a through hole.

Inside the through hole of the end plate 203 of the transport container 20, there is attached a stainless steel support tube 300 which is provided with a cylinder-shaped seal member 301 made of porous silicone and a retainer ring 302 to retain the seal member 301.

Figure 2:
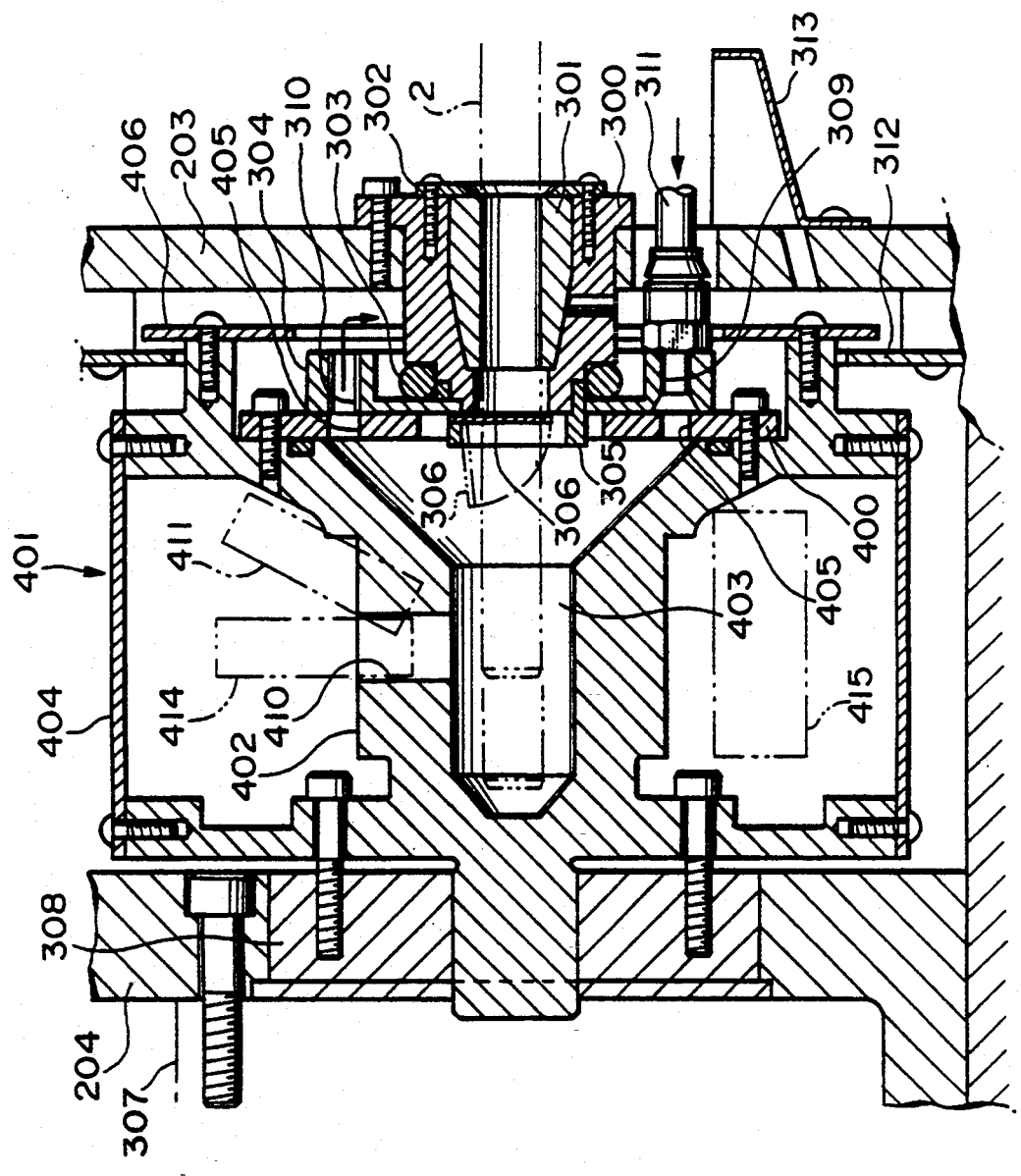
FIG. 2 is a cross sectional view of the main portion of FIG. 1.

As shown in FIG. 2, the support tube 300 is narrow tipped, and the tip end is provided with a ring shaped rubber member 303, and a ring shaped contact member 304 (immobile or non-rotating lid member) made of plastic. The elastic force of the ring shaped rubber member 303 forces the contact member 304 towards the tip end of the support tube 300. Also at the tip end of the support tube 300, there is an lid member 306 engaged with a lid support frame 305 so as to be freely openable by swinging upwards.

Opposing the contact member 304, a ring-shaped rotating lid member 400 made of stainless steel is freely slidably disposed, and the sliding surface of the rotating lid member 400 against the contact member 304 is coated with Teflon (tetrafluoride resin). The rotating lid member 400 is attached to the opening section of a funnel-shaped inspection section 403 formed on a main body 402 of the rotating member 401. The rotating member 401 includes a cylinder member 404 disposed around the main body 402, and the main body 402 is attached to the hollow rotation section 308 of the air bearing 307 fixed to the through hole of the mid section plate 204.

The rotating lid member 400 has a plurality of flow passages 405 around its periphery, and opposite to the flow passages 405 at the upper and the lower sections of the contact member 304, there are formed a supply passage 309 to supply water to the inspection section 403 of the rotating member 401, and an collection passage 310 for collecting the water flowing out of the inspection section 403. The flow passage 405 side of the supply passage 309 is shaped so that the diameter of the passage expands towards the end, and the diameter of the expanded end section of the supply passage 309 is made larger than the inside diameter of the flow passage 405.

Furthermore, the inside diameters of the supply passage 309 and the collection passage 310 are chosen to be larger than the distance between the two adjacent flow passages 405. The supply passage 309 is connected to a supply pipe 311, and the water supplied via the supply pipe 311 fills the inspection section 403 via the supply passage 309 and the flow passage 405, and the water from the inspection section 403 of the rotating member 401 flows downstream via the flow passage 405 and is collected via the collection passage 310.

There is an interference plate 406 provided on the main body 402 of the rotating member 401, and opposing the interference plate 406, there is an interference plate 312 provided on the transport container 20. The numeral 313 refers to a drain receptor disposed on the end plate 203.

On the rotation section 308 of the air bearing 307, there is attached a pulley 315 via a hollow attachment member 314, and the pulley 315 is connected with a pulley 317 via a belt 316. The pulley 317 is attached to the rotation shaft of the motor 318 disposed on the lower surface of the lower plate 200 via a bracket 319. By rotating the rotation shaft of the motor 318, the pulley 317, the belt 316 and the pulley 315 are rotated and thereby rotating the rotating member 401 around its axis.

Figure 3:
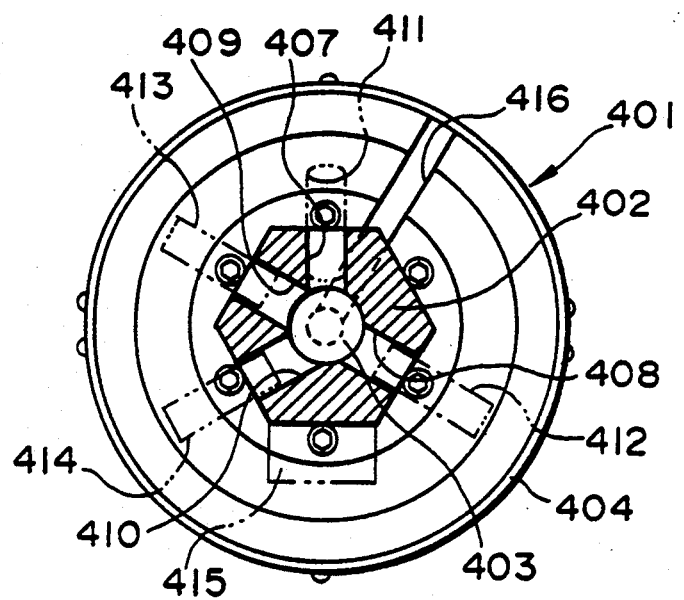
FIG. 3 is a cross sectional view of a plane taken through the line III—III in FIG. 1.
Figure 4:
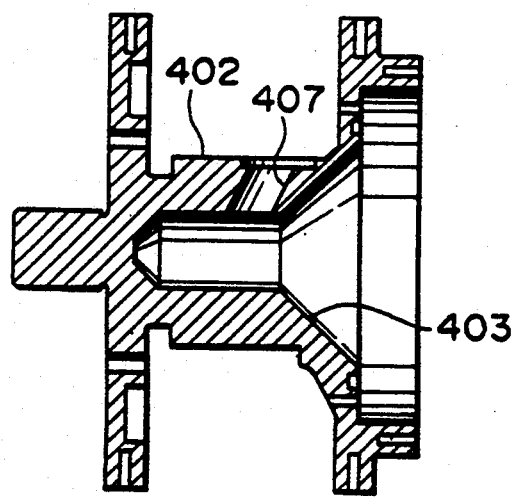
FIG. 4 is a cross sectional view of the main member of a rotation body.
Figure 5:
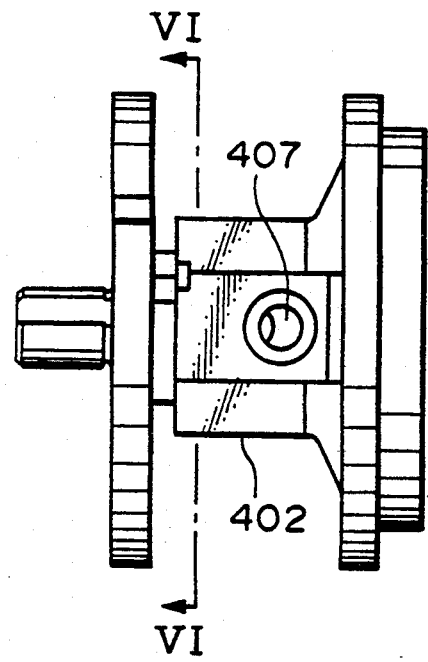
FIG. 5 is a side view of a main member of the rotation body.

As shown in FIG. 3, on the main body 402 of the rotating member 401, there are formed four probe holes 407, 408, 409 and 410 which passes through to the inspection section 403 from the outer periphery. In each of the four probe holes 407–410, there is disposed a probe 411 for detecting melting deficiency, a probe 412 for detecting defects in the seal section, a high frequency probe 413 for detecting porosity undercut and a probe 411 for detecting defects in the shallow section.

Figure 11:
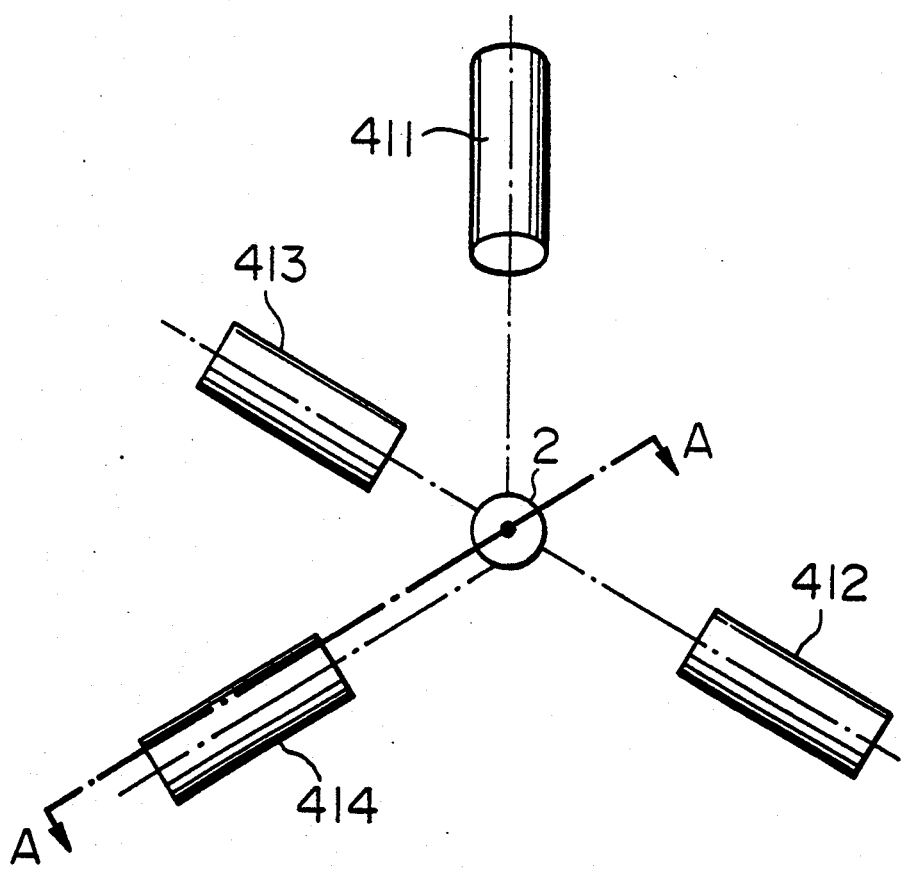
FIG. 11 is a view to illustrate the arrangement of the detection probe around the weld of the fuel rod.
Figure 12A:
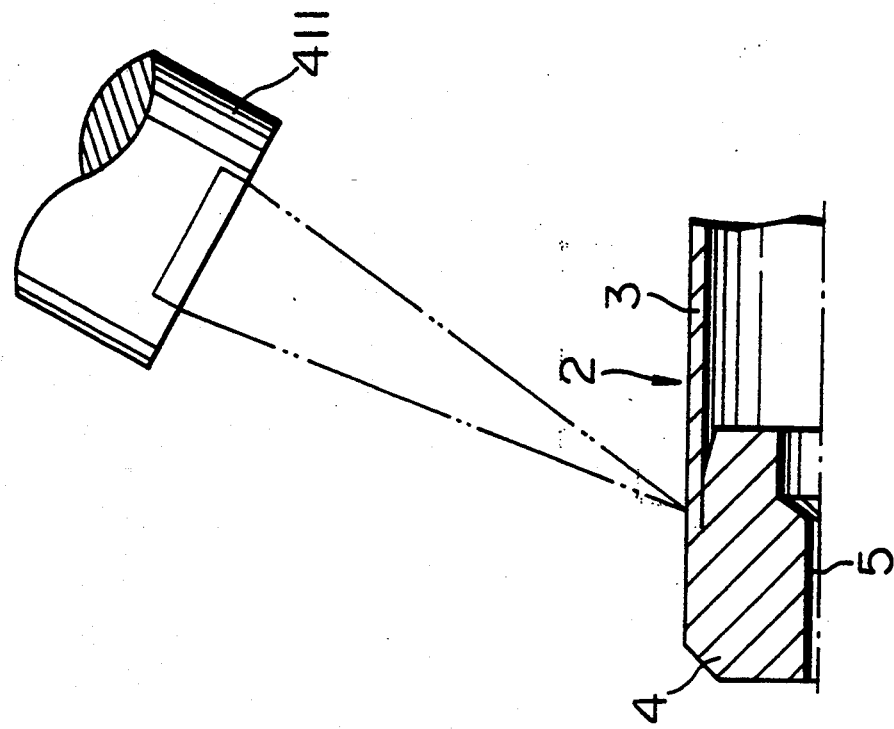
FIG. 12 (a) is a cross sectional view of the weld section to illustrate the arrangement of a probe for detecting melting deficiency.
Figure 12B:
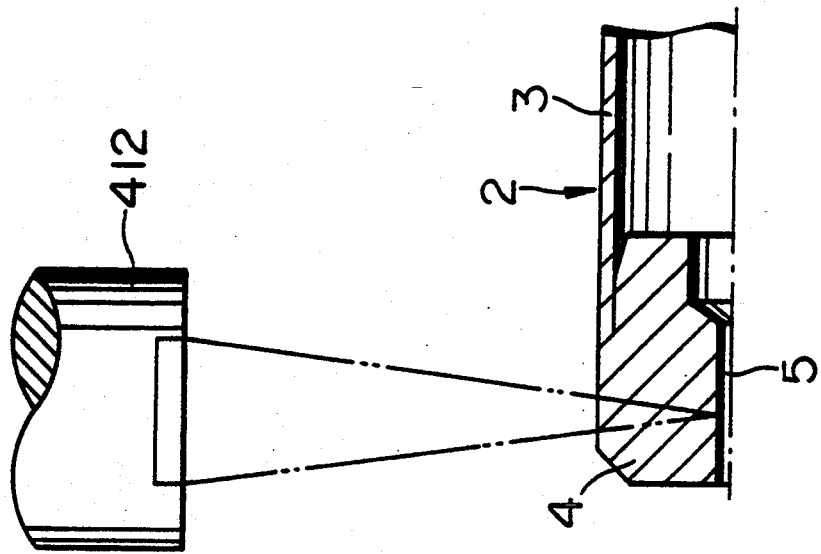

The melt deficiency probe 411 is used to detect insufficient melting between the end plug and the edge of the fuel pipe 3 of the fuel rod 2. As shown in FIGS. 11 and 12 (a), the probe 411 is disposed so that the axial line of the probe 411 lies in a plane which includes the rotational axis of the rotating member 401 (i.e the axis of the fuel rod 2), and is inclined at an angle to the rotational axis.

The probe 412 for detecting defects in the seal section is used to search for the welding condition of the gas seal hole 5 formed in the center section of the end plug 4. This probe is also disposed so that the axis of the probe 412 crosses the rotational axis of the rotating member 401 as shown in FIGS. 11 and 12 (b).

Figure 13A:
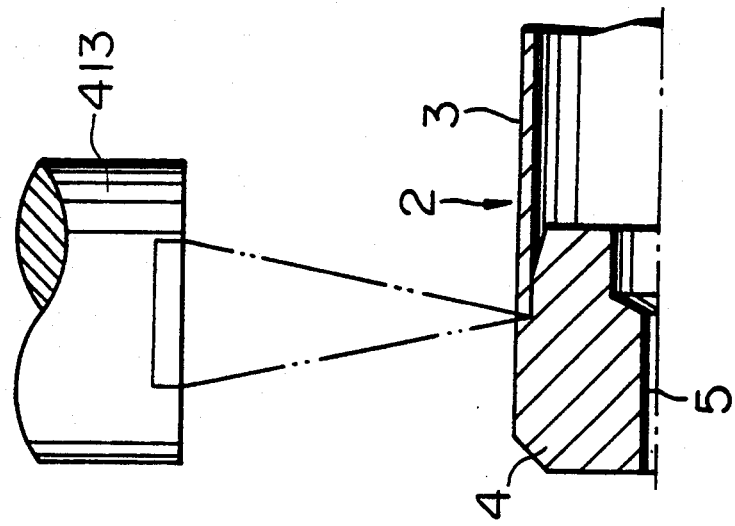
FIG. 13 (a) is a cross sectional view of the weld section to illustrate the arrangement of a probe for high frequency detection of porosity and undercut; and FIG. (b) is a cross sectional view at line A—A in FIG. 11 of a probe for detecting defects in the shallow section.
Figure 13B:
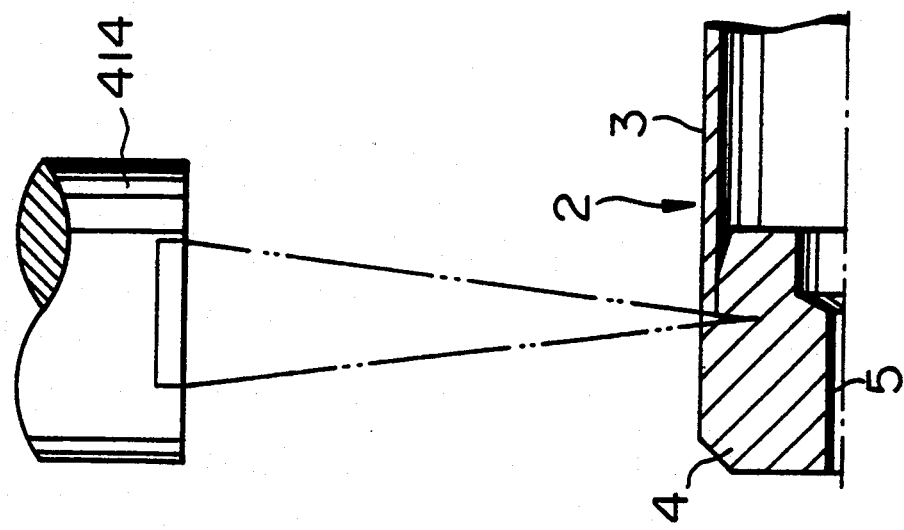

The high frequency probe 413 for detecting defects in the porosity undercut is used to search for porosity defects and undercut defects in the welds. As shown in FIGS. 11 and 13 (a), the probe 413 is disposed opposite to the axis of the probe 412, and is spaced a specific distance away from the probe 412 along the rotational axis. The probe 413 is connected electrically to the preamplifier 415 disposed in the rotating member 401 as shown in FIG. 3.

The probe 414 for detecting porosities in the shallow section supplements the probe 413, and is used to search for defects in the surface section of the weld periphery. The probe 414 is disposed as shown in FIGS. 11 and 13 (b) so that its axis lies in the plane perpendicular to the rotation axis of the rotating member 401 (axis of the fuel rod), and is directed towards the outer periphery of the fuel rod 2 away from the center of the rotating member 401.

Figure 6:
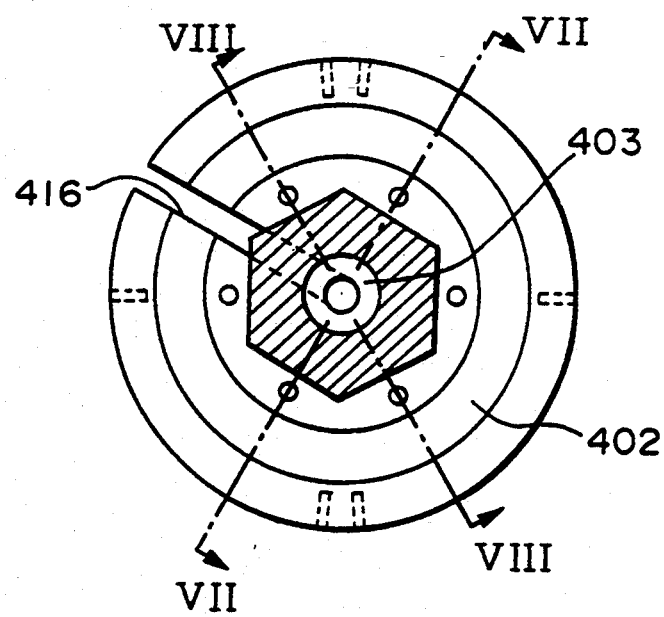
FIG. 6 is a cross sectional view of a plane taken through the line VI—VI in FIG. 5.
Figure 7:
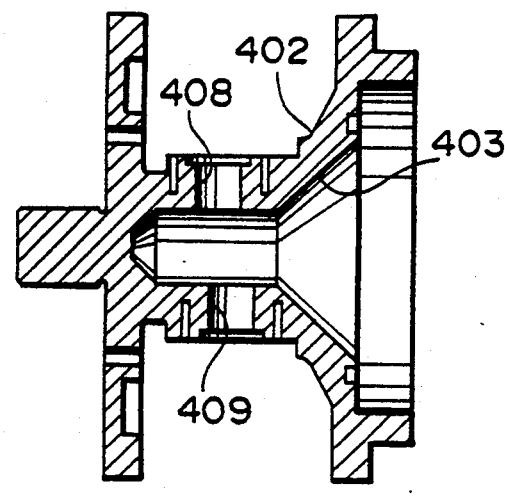
FIG. 7 is a cross sectional view of a plane taken through the line VII—VII in FIG. 6.
Figure 8:
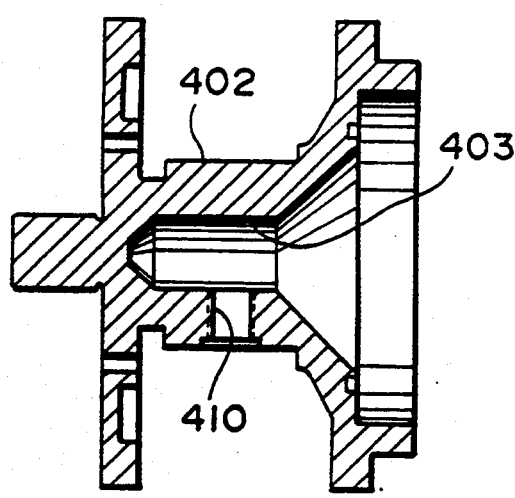
FIG. 8 is a cross sectional view of a plane taken through the line VIII—VIII in FIG. 6.
Figure 9:
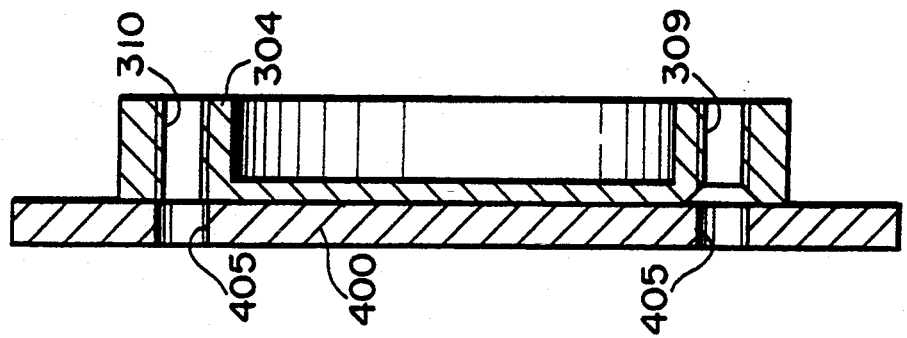
FIG. 9 a cross sectional view of a rotation lid member and a sliding member.
Figure 10:
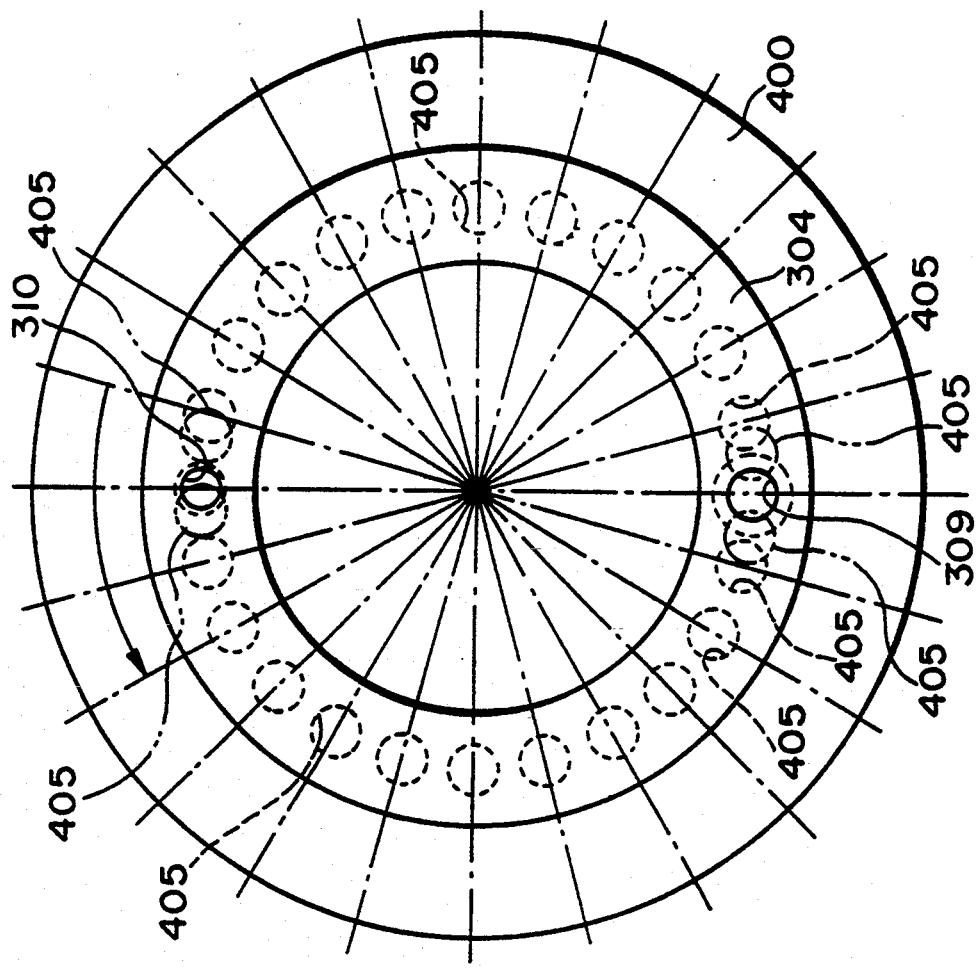
FIG. 10 is a side view of the section shown in FIG. 9.

The lead wires for each of the probes 411–414 and the preamplifier 415 are passed through a groove section 416 formed in the main body 402, as shown in FIG. 6, and are led to the rotary connector 417 attached to the hollow attachment section 314 via the rotation section 308 of the air bearing 307 and the interior of the hollow attachment section 314. The electrical signals from the probes 411–414 are sent through the rotary connectors 417 to the outside analyzer. As illustrated in FIG. 1, the rotary connector 417 is fixed to the lower plate 200 by means of wire 320 for preventing the rotation.

As shown in FIG. 1, there is a chuck device 6 disposed on the support member 8 erected on the base 1 on the outside of the end plate 203, for fixing in place the fuel rod 2 after it is transported along its axis. Above the fuel rod 2 held in the chuck device 6, there is a laser operated feed meter 7 for detecting the travel distance along the axial direction of the fuel rod 2.

Next, the operation of the ultrasonic detection device of the above-described configuration will be presented. First, by rotating the rotation shaft of the motor 318, the rotating member 401 is rotated around its axis (e.g. at 10 rotations per second) via the pulley 317, the belt 316, the pulley 315, the hollow attachment section 314 and the rotation section 308 of the air bearing 307.

At the same time, the inspection section 403 is filled with water through the supply pipe 311, the supply passage 309 of the contact member 304 and the flow passage 405 of the rotating lid member 400. With the chuck device 6 in the open state, the fuel rod to be examined is transported along its axis, and is inserted inside the seal member 301 of the support tube 300 so as to push open the lid member 306 until the welded section of the fuel rod 2 is housed in the inspection section 403.

In this case, until the fuel rod 2 is inserted into the inspection section 403, the lid member 306 closes the tip end of the support tube 300. After the fuel rod 2 is inserted in the inspection section 403, the fuel rod 2 is enveloped tightly with a seal member 301 made of porous silicone, and the elastic force of the ring shaped rubber member 303 forces the contact member 304 against the rotating lid member 400. The configuration described above is effective in preventing leaking of the water from anywhere except from the collection passage 310, and the water in the inspection section 403 flows out through the flow passage 405 of the rotating lid member 400 and is collected from the collection passage 310 of the contact member 304 to be returned to the pump to be recirculated.

The water supply to the inspection section 403 is assured by having the configuration as follows. The supply passage 309 on the flow passage 405 side is made so that the diameter expands towards the end, and the expanded section of the supply passage 309 is made larger than the inside diameter of the flow passage 405, and the inside diameter of the supply passage 309 is made larger than the distance between the two adjacent flow passages 405. Therefore, regardless of the positions of the rotating member 401 and the rotating lid member 400, the water is supplied reliably to the inspection section 403 of the rotating member 401 through the supply passage 309 of the contact member 304.

Further, because the inside radius of the collection passage 310 is made to be larger than the distance between the two adjacent flow passages 405, even while the rotating lid member 400 is rotating, the water flowing out of the inspection section 403 of the rotating member 401 through the flow passage 405 is always collected from the collection passage 310 of the contact member 304, thereby smoothly removing the air bubbles mixed in with the water filling the inspection section 403.

While the fuel rod 2 is being inserted into the inspection section 403, the analyzer is used to monitor the reflecting surface waves to detect the tip of the fuel rod 2. After the tip of the fuel rod 2 is detected, the fuel rod 2 is moved forward a specific distance which is measured by the laser operated feed meter 7, and is fixed in the inspection position by means of the chuck device 6.

Next, the entire periphery of the welded section of the fuel rod 2 is examined with the rotating probes 411–414, to perform the detection of melting deficiency, seal section defects, high frequency search of porosity and undercut and the shallow section. During the inspection process, the position of the transport container 20 is adjusted suitably by operating the transport motor 101 to move the coupling 102, ball screw shaft 103 and the nut section 105.

By moving the components in the transport container 20, such as the rotating member 401, rotating lid member 400 and the contact member 304, seal member 301 and the support tube 300 a specific distance (e.g. 1 mm) with respect to the fuel rod 2, it becomes possible to inspect a corresponding specific distance in the welded section of the fuel rod 2 rapidly and with high resolution.

The detection signals from the probes 411–414 are led through the groove section 416 in the main body 402 of the rotating body 401, rotation section 308 of the air bearing 307 and the hollow attachment section 314, and are led to the rotary connector 417 to be forwarded outside to the analyzer.

When an ultrasonic inspection of one fuel rod 2 is thus completed, the chuck device 6 is released, and the fuel rod 2 is pulled out of the inspection section 403, and a next fuel rod 2 is inserted therein.

The inspection process presented above enables to load and discharge the fuel rod 2 to and from the inspection section 403 through the seal member 301 of the support tube 300 and lid member 306 supported by the lid support frame 305 while rotating the probes 411–414 continuously. Therefore the inspection process has been greatly simplified, and even during the inspection process, the fuel rod 2 is firmly gripped and fixed in place by the chuck device 6 as well as supported firmly by the seal member 301, thus avoiding contact with the rotating member 401 or the rotating lid member 400 and assuring that there will be no damage inflicted on the surface of the fuel rod 2.

What is claimed is:

1. An inspection device for examining defects in a welded section of a fuel rod comprising:
   (a) a rotating member freely rotating around a rotation axis, said rotating member having an inspection section within which said fuel rod is at least partially disposed during inspection;
   (b) a liquid supplying means for filling a liquid medium in said inspection section;
   (c) a plurality of ultrasonic probes disposed on said rotating member having said inspection section, and wherein said inspection section is disposed radially inside of said plurality of probes in said rotating member.

2. A device as claimed in claim 1, further comprising a chuck mechanism for holding the fuel rod immobile.

3. A device as claimed in claim 1 wherein said rotation axis is arranged horizontal.

4. A device as claimed in claims 2, wherein said chuck mechanism holds fuel rod coaxially to said rotating member.

5. A device as claimed in claim 1, wherein said device is provided with a transport device which moves said rotating member in an axial direction relative to said fuel rod along the rotation axis.

6. A device as claimed in any of claims 1 to 5, wherein a non-rotating lid member is provided opposite to and in sliding contact with an opening section of said rotating member for supporting said fuel rod which passes through a through hole disposed on said non-rotating lid member.

7. A device as claimed in claim 6, wherein said through hole is provided with: a seal member which envelopes said fuel rod tightly; and a lid member which closes said through hole and swings inside the inspection section to open when the fuel rod is inserted through said through hole.

8. A device as claimed in claim 6, wherein said liquid supply means is disposed on a lower part of said non-rotating lid member, and a liquid collection means for collecting liquid flowing out of said inspection section is disposed on an upper portion of said inspection section disposed on an upper portion of said non-rotating lid member.

9. A device as claimed in claim 8, wherein a plurality of liquid flow passages are provided on a rotating lid member at an outer periphery of said rotating lid member; and liquid supply passages are provided opposite to each of said liquid flow passage disposed on the lower part of said non-rotating lid member for supplying liquid to said inspection section of said rotating member; and the liquid collection passages are provided on the upper part of said non-rotating lid member opposite to each of said liquid flow passages for collecting liquid flowing out of said inspection section of said rotating member; wherein the diameters of each of said liquid supply passages and liquid collection passages are larger than the distance between two adjacent liquid flow passages.

10. An inspection device for examining defects in a welded section of a fuel rod comprising:
   (a) a rotating member freely rotating around a rotation axis and having an inspection section within which said fuel rod is at least partially disposed during inspection;
   (b) a plurality of ultrasonic probes disposed on said rotating member having said inspection section, and wherein said inspection section is disposed radially inside of said plurality of probes in said rotating member;
   (c) a non-rotating lid member provided opposite to and in sliding contact with an opening section of said rotating member, and wherein said fuel rod passes through a hole disposed on said non-rotating lid member;
   (d) said non-rotating lid member including at least one liquid supply passage through which liquid is supplied to said inspection section and at least one liquid collection passage through which liquid is removed from said inspection section.

11. The inspection device of claim 10, further including a rotating lid disposed on said rotating member, said rotating lid including a plurality of liquid flow passages which communicate with said at least one liquid supply passage and said at least one liquid collection passage of said non-rotating lid member.

12. The inspection device of claim 10, further including a transport device which moves said rotating member in an axial direction relative to said fuel rod along the rotation axis.

13. The inspection device of claim 1, wherein said inspection section is in the form of a chamber having a first closed end and a second end axially spaced from said first end, with said second end including a lid having liquid flow passages therein.

* * * * *